United States Patent [19]

Coats et al.

[11] Patent Number: 4,574,194

[45] Date of Patent: Mar. 4, 1986

[54] METHOD AND APPARATUS FOR MONITORING THE MANUFACTURE OF A TWO-COMPONENT WEB

[75] Inventors: Montgomery R. Coats, Edmond; Dawn E. Holt, Oklahoma City, both of Okla.

[73] Assignee: Fife Corporation, Oklahoma City, Okla.

[21] Appl. No.: 547,628

[22] Filed: Nov. 1, 1983

[51] Int. Cl.[4] .......................................... G01N 23/16
[52] U.S. Cl. ................................ 250/308; 250/358.1; 250/505.1; 378/53
[58] Field of Search ....................... 378/53, 54, 55, 56; 250/308, 358.1, 359.1, 360.1, 505.1

[56] References Cited

U.S. PATENT DOCUMENTS

| | | |
|---|---|---|
| 3,082,323 | 3/1963 | Chope et al. . |
| 3,087,061 | 4/1963 | Dukes et al. . |
| 3,452,192 | 6/1969 | Hanken . |
| 3,500,446 | 3/1970 | Hasegawa et al. ................. 250/308 |
| 3,665,199 | 5/1972 | Cahill et al. . |
| 3,889,121 | 6/1975 | Bossen ................................ 250/308 |
| 4,182,954 | 1/1980 | Giles .................................. 250/359.1 |

OTHER PUBLICATIONS

Mladjenovic, Radioisotope and Radiation Physics, 1973, Academic Press, N.Y., sections 6.8.2 through 6.10, pp. 153–159.
Tsoulfanidis, "Measurement and Detection of Radiation", McGraw-Hill Book Co., N.Y., 1983, p. 117.

Primary Examiner—Alfred E. Smith
Assistant Examiner—Carolyn E. Fields
Attorney, Agent, or Firm—Dunlap, Codding & Peterson

[57] ABSTRACT

A beta radiation sensor and an X-ray radiation sensor are used to monitor the specific weights of both components of a two-component web, in particular, a web of magnetic recording material, by using the beta radiation sensor to measure the combined specific weight of the material. The measurement by the X-ray sensor permits such combined specific weight to be apportioned between the two components of the web. Cross talk between the two sensors arising from bremstrahlung produced by the beta radiation sensor is suppressed by softening the beta radiation beam with films of polyester, by shielding the housing in which the detectors of the two sensors are disposed with a sheet of phenolic, and by stopping down the aperture through the sheet of phenolic through which X-ray radiation enters the detector housing.

38 Claims, 4 Drawing Figures

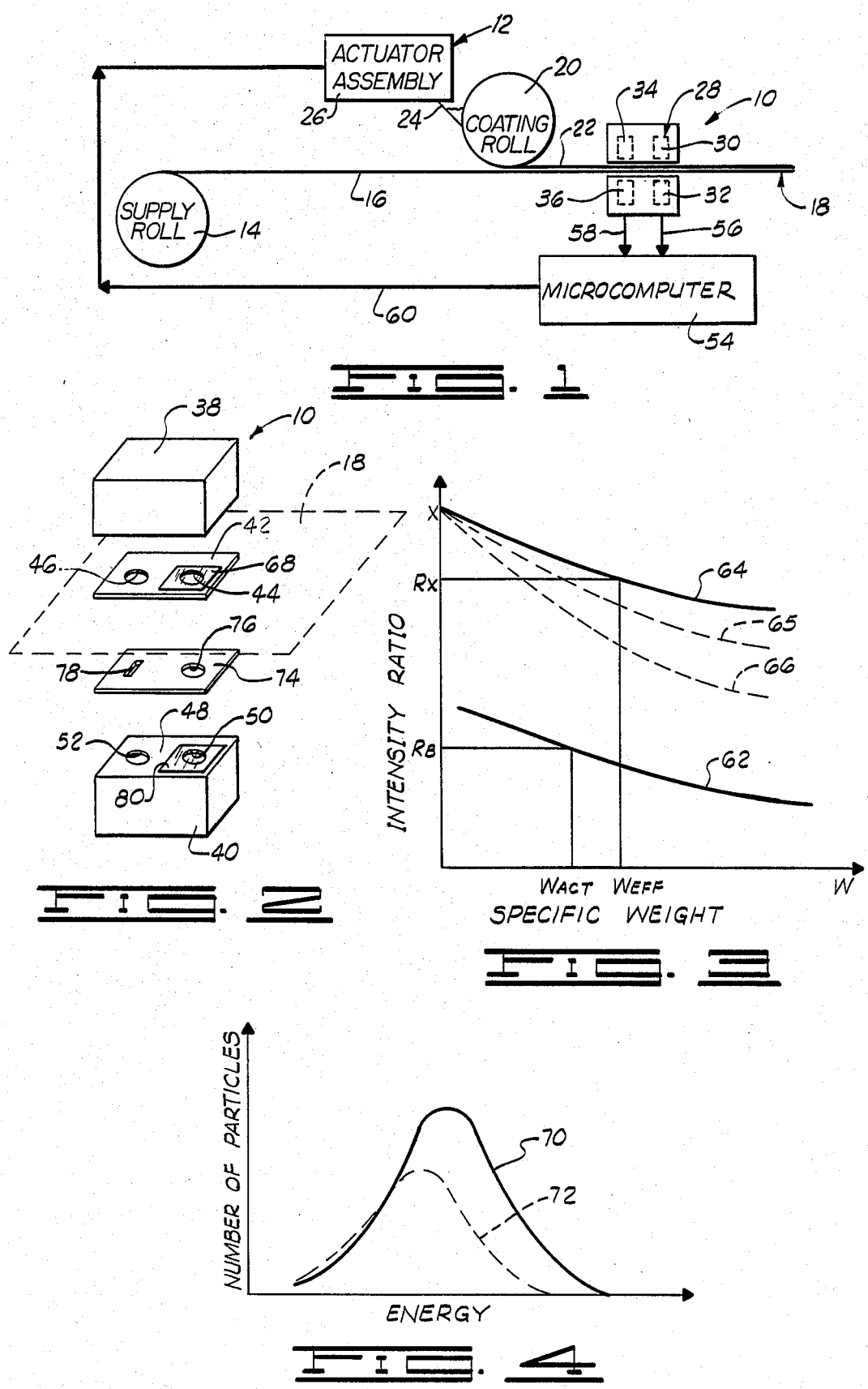

METHOD AND APPARATUS FOR MONITORING THE MANUFACTURE OF A TWO-COMPONENT WEB

BACKGROUND OF THE INVENTION

1. Field of the Invention

The present invention relates generally to the manufacture of layered webs comprised of more than one component material and, more particularly, but not by way of limitation, to the manufacture of webs of magnetic recording material comprised of a dielectric film coated with a binder containing a magnetic material.

2. Brief Discussion of the Prior Art

Consumer and industrial goods include a wide variety of products which have the general form of a composite built up of thin layers of two different materials. For example, magnetic recording tape commonly consists of a thin strip of polyester coated on both sides with a layer of epoxy containing ferric oxide. These composites can be manufactured by a variety of techniques; for example, by various coating techniques in which a plasticized layer of one material is deposited on a moving web of the other material. Similarly, the product can, in some cases, be manufactured by simultaneously extruding the two materials in the form of two webs in contact. In any event, it is common practice to form very wide webs of these composites which are later cut to a desired shape or width to minimize the cost of manufacturing the product.

For the ultimate product to serve its intended purpose, the thicknesses of the layers must meet standards which are often embodied in a requirement that the specific weight; that is, the weight per unit area, of each of the two components of the web is to lie within preselected limits. In order to meet these standards, the specific weights are measured during the manufacture of the web so that the machinery used in the manufacture can be adjusted to maintain the preselected specific weights for the components of the web. A device that is commonly used in the measurement of the specific weight of a web is a radiation sensor that includes a source of radiation that can be placed on one side of the web and a radiation detector that can be placed on the other side of the web to provide a signal that is a measure of the attenuation of a beam emitted by the source as the beam passes through the web. Such a signal can be converted to a specific weight signal that can be transmitted to a display or a control device so that the machinery which produces the web can be either manually or automatically adjusted to cause the web to meet the required standards.

In the past, the monitoring of specific weights of the components of a composite web has often been carried out by measuring the absorption of radiation by a web formed of one of the components followed by a similar measurement on the web after the second component has been added to the web. This approach has several disadvantages. For economy of manufacture, the web width will often be very large so that the web must be scanned by moving the radiation sensor back and forth across the width of the web in order to monitor the specific weights of the web components throughout the width. The cost of the machinery to effect this scanning is by no means inconsequential. Moreover, separate scanning of the one-component web and the finished product necessarily requires that the two sensors used for this purpose make measurements on widely spaced portions of the web. This spacing can result in appreciable lengths of non-standard web being produced before a divergence from tolerances can be detected and corrected. Because of these problems, it would be preferred to have only one device, including two sensors located together immediately downstream of the machinery which completes the web manufacturing process, to make the specific weight determinations.

However, the inclusion of several sensors in one scanning head that traverses only the finished product also presents problems. In general, both sensors will respond to both materials of which the web is comprised so that calibration of an assembly of sensors to yield both specific weights can be difficult and may require the acceptance of approximations that detract from the ability of the assembly to accurately measure the specific weights of the two web components. Moreover, where several sensors are mounted on one scanning head, cross talk between the sensors can become a problem. That is, the detector of one sensor responds to radiation produced by the source of the other sensor so that the signal produced by such detector does not provide an accurate measure of the effect of the web on the radiation beam that the detector is designed to receive. Moreover, the mechanism by means of which the cross talk occurs can involve the interaction of the radiation beams of the sensors with the web itself so that calibration of the sensors to compensate for cross talk can become a difficult proposition.

SUMMARY OF THE INVENTION

The present invention overcomes these problems to provide a method and apparatus for accurately monitoring the specific weights of both components of a two-component web using a single scanning head that can be positioned immediately downstream of the final device used in the manufacture of the web. The scanning device includes two radiation sensors, each of the radiation sensors being comprised of a radiation source and a radiation detector, and one aspect of the invention lies in the characteristics of the radiation produced by the sources used in these sensors. In particular, the source chosen in a first one of these sensors is selected so that the radiation beam produced by such source is affected in substantially the same manner by both components of the web. In one important application of the invention, in which the invention is used to monitor the specific weights of the two components of magnetic recording material during the manufacture of the material, the source of the first sensor directs a beam of beta radiation through the finished web to an ionization detector which produces a signal proportional to the number of beta particles received by the detector. It has been found that the attenuation of the beta radiation beam in the web is substantially independent of the relative specific weights of the two web components so that the signal produced by the detector of the first radiation sensor can be related to the combined specific weights of the two components of the finished web.

The radiation source in the second of the two radiation sensors is selected so that one of the materials that comprise the web absorbs the radiation beam of the second sensor more strongly than the other material but the absorption in both materials depends exponentially on the specific weight of each layer of the material traversed by the second radiation beam. Using radiation sensors so selected and a microcomputer, signals indicating the specific weights of both components of the web can be readily generated. These signals can be transmitted to a display device for manual control of the web manufacturing equipment or to actuators which control the manufacturing process automatically. In the application of the invention referred to above in which the invention is adapted to the manufacture of magnetic recording material, it has been found that the second radiation sensor can be a sensor in which a beam of X-rays is directed through the web.

In a second aspect of the invention, cross talk between the two sensors in the sensor assembly, such sensors being located in the scanning head that is moved back and forth across the width of the finished web, is suppressed by beam softening, shielding and beam limiting techniques directed toward the reduction of bremstrahlung in a system including a beta ray source and an X-ray detector. In the practice of the invention to include the second aspect, the sources for both sensors are placed in a source housing disposed to one side of the web and the detectors are placed in a detector housing positioned parallel to the source housing on the other side of the web. Apertures are provided through facing walls of the two housings so that the source of each sensor can direct a beam of radiation through an aperture in the source housing wall, through the web, and through an aperture in the detector housing wall to the detector. In order to reduce cross talk between the two sensors, arising primarily from the generation of bremstrahlung by the beta ray beam that can be detected by the X-ray detector, the beta ray beam is softened as it leaves the source housing and as it enters the detector housing. Such softening is accomplished, without the production of bremstrahlung, by means of polyester films that are placed across the source and detector housing apertures through which the beta radiation beam passes. In order to prevent the production of bremstrahlung by beta radiation scattered from the beam by the web and impinging upon the detector housing, the side of the detector housing facing the source housing is covered with a detector housing shield that prevents beta particles scattered from the beta sensor beam by the web from impinging upon the detector housing to produce bremstrahlung at the surface of such housing. In order to prevent appreciable bremstrahlung from being produced in the detector housing shield, such shield is constructed of an organic polymer such as the phenolic material used in the manufacture of printed circuit boards. In addition, the aperture formed through the detector housing shield to transmit the radiation beam of the X-ray sensor is shaped to limit the directions from which radiation can enter the beam aperture formed through the detector housing to admit X-ray radiation into such housing. Thus, the X-ray aperture formed through the detector housing shield is made smaller than the corresponding X-ray aperture formed through the detector housing wall and is shaped to exclude bremstrahlung produced by beta particles from the beta source used in the beta radiation sensor while not interfering with the passage of the beam of the X-ray sensor into the detector housing.

An important object of the present invention is to provide a method and apparatus for accurately monitoring the specific weights of both components of a two-component web.

Another aspect of the invention is to provide a system of bremstrahlung suppression that will permit an X-ray sensor to be used in close proximity to a beta radiation sensor.

Yet another object of the invention is to provide a method and apparatus for monitoring the specific weights of the components of a web that utilizes only one scanning mechanism to move radiation detectors back and forth across the width of the web.

Other objects, advantages and features of the invention will become clear from the following detailed description of the preferred embodiment of the invention when read in conjunction with the drawings and appended claims.

BRIEF DESCRIPTION OF THE DRAWINGS

FIG. 1 is a schematic diagram illustrating the mounting of the apparatus of the present invention on a web manufacturing machine.

FIG. 2 is a partially exploded view of the sensor assembly shown in FIG. 1.

FIG. 3 is a graphical representation of the characteristics of the radiation sensors used in the present invention.

FIG. 4 is a graphical representation of the effect of beam softening on the energy distribution of beta radiation.

DESCRIPTION OF THE PREFERRED EMBODIMENT

As has been noted above, an important application of the present invention is the use of the invention to monitor the production of magnetic recording material which is comprised of a dielectric substrate and a magnetic coating. For purposes of illustration of the invention, it will be useful to consider this specific application of the invention and, further, a specific manner of producing the recording material. However, it will be recognized by those skilled in the art that the invention is not limited to this particular application nor to any particular web manufacturing machine; rather, the description of this application and the machinery the application involves is merely for purposes of providing a clear teaching of the invention.

Referring first to FIG. 1, shown therein and designated by the general reference numeral 10 is a schematic representation of an apparatus for generating signals indicative of the specific weights of both components of a web of magnetic recording material. The machine used to produce the web, schematically indicated at 12, comprises a roll 14 from which a starting web 16, forming a portion of a finished web 18, can be drawn. The starting web 16 can be a dielectric substrate, such as polyester, or a dielectric substrate which has previously been coated on its underside, as seen in FIG. 1, with a layer of a magnetic material, such as ferric oxide, in an appropriate binder such as epoxy. The finished web 18 can thus be the substrate coated on one side or both sides.

The web 16 passes under a roll 20 which deposits a layer 22 of the binder and magnetic material on the upper surface of the starting web 16 to form the finished web 18. A doctor knife 24 positioned by a conventional actuator assembly indicated schematically at 26 in FIG. 1, controls the quantity of magnetic coating that is placed on the coating roll 20 to control the thickness of the layer 22 that is deposited on the web 16. Thus, the finished web 18 is a two-component web containing a layer of the dielectric and either one or two layers of the magnetic coating.

In general, the apparatus 10 is comprised of a sensor assembly 28 that is mounted on a scanning device (not shown) located immediately downstream of the coating roll 20 so that the apparatus 10 can be moved back and forth across the width of the finished web 18 in a conventional manner. In addition, and for reasons that will become clear below, the sensor assembly 28 can be moved off the web 18. The sensor assembly 28, in turn, is comprised of a first radiation sensor (not numerically designated in the drawings) which includes a first radiation source 30 that directs a first radiation beam through the finished web 18 to a first radiation detector 32 disposed on the side of the web 18 opposite the side of the web 18 to which the radiation source 30 is disposed. In the particular application in which the finished web 18 is a web of magnetic recording material, a suitable source for the first radiation sensor is a low-to-medium energy beta radiation source having an energy range of about 0.07 mev to about 0.7 mev. An example of such a source is a krypton 85 encapsulated isotopic source. With beta radiation in such an energy range, the transmitted intensity of the first radiation beam will be sufficient to be measured and will be sufficiently reduced from the incident intensity to provide an accurate measure of the specific weight of the web. The beta radiation source produces a beam which is then collimated and directed toward the upper surface of the web 18. The sensor assembly 28 further comprises a second radiation sensor (not numerically designated in the drawings) which includes a second radiation source 34 that directs a second radiation beam through the web 18 to a second radiation detector 36 disposed across the web from the radiation source 34 in the same manner that the first radiation detector 32 is disposed across the web from the first radiation source 30. In the particular application in which the finished web 18 is a web of magnetic recording material, a suitable source for the second radiation sensor is an X-ray source having a photon energy range of from about 3.5 kev to about 15.0 kev. Such a source will provide transmitted intensities suitable for accurately measuring the specific weight of the magnetic recording material. A particularly suitable source is an iron 55 encapsulated isotopic source which produces monoenergetic photons at 5.9 kev. Photons of this energy correspond closely to the K absorption edge of metallic elements of which magnetic materials used in recording material are comprised. As a result, the magnetic coating being measured will have a high attenuation coefficient compared to that of the dielectric substrate but the energy of the photons will be high enough to avoid absorption by air and beryllium windows with which X-ray detectors are often provided. The X-ray source produces a beam of X-rays which is collimated and directed toward the web 18 so that the second radiation beam is directed toward the second radiation detector 36.

In order to position the sources 30 and 34 and the detectors 32 and 36 about the web 18, the apparatus 10 comprises a source housing 38, in which the sources 30 and 34 are disposed, and a detector housing 40, in which the detectors 32 and 36 are disposed, the housings 38 and 40 being schematically illustrated in FIG. 2. Each of the housings 38 and 40 has the general form of a metal box including one wall through which apertures are formed to permit passage of the first and second radiation beams from the sources 30, 34 to the detectors 32, 36. In particular, the wall 42 of the source housing 38 that faces the web 18, shown in dashed lines in FIG. 2, is provided with a first beam aperture 44 above which the first radiation source 30 is disposed and a second beam aperture 46 above which the second source 34 is disposed. Similarly, the wall 48 of the detector housing 40 that faces the web 18 is provided with a first beam aperture 50 through which the first radiation beam passes and a second beam aperture 52 through which the second radiation beam passes. (When the sources for the sensors are the beta ray and X-ray sources referred to above, the first beam apertures 44 and 50 will sometimes be referred to as beta ray beam apertures and the second beam apertures 46 and 52 will sometimes be referred to as X-ray beam apertures.) When the apparatus 10 is mounted on a scanning apparatus, the housings 38, 40 are positioned, as indicated in FIGS. 1 and 2, so that the housings 38 and 40 extend parallel to each other in a spaced-apart relation with the apertured wall 48 of the detector housing facing the apertured wall 42 of the source housing, with the first beam aperture 44 through the wall 42 aligned with the first beam aperture 50 through the wall 48, and with the second beam aperture 46 aligned with the second beam aperture 52. Thus, the first radiation beam is emitted by the first source 30, passes through the first beam aperture 44 through the wall 42 of the source housing, passes through the web 18, and then enters the first beam aperture 50 through the wall 48 of the detector housing to impinge upon the first detector 32 and the second radiation beam emitted by the second source 34 passes through the second beam aperture 46 through the wall 42 of the source housing 38, through the web 18, and enters the detector housing 40 through the second beam aperture 52 formed through the wall 48 of the detector housing 40 to impinge upon the second detector 36.

In addition to the sources 30, 34 and the detectors 32, 36, the apparatus 10 further comprises a microcomputer which has been schematically indicated at 54 in FIG. 1. The microcomputer 54 receives signals from the detectors 32 and 36 on signal paths 56 and 58 and outputs a signal indicative of the specific weights of the two components of the web 18 on a signal path 60. In some circumstances, the signal path 60 will extend to an actuator assembly as has been shown in FIG. 1 in which the signal path 60 extends to the actuator assembly 26 to provide for automatic control of the process in which the layer 22 is deposited on the web 16. However, it is also contemplated that the apparatus 10 will be used to monitor the manufacture of the web 18 and, in such case, the signal path 60 extends to a display device (not shown) to provide a numerical indication of the specific weights of both components of the web 18. In this latter case, the actuator assembly 26 can be operated manually to adjust the thickness of the layer 22 that is deposited on the web 16.

MEASUREMENT OF SPECIFIC WEIGHT

FIG. 3 has been provided to illustrate the manner in which the apparatus 10 is utilized to obtain signals that indicate the specific weights of the two components of the web 18. In particular, FIG. 3 illustrates calibration curves which are programmed into the microcomputer 54 to permit the specific weight indicator signals to be generated in the microcomputer 54 from detector signals provided by the detectors 32 and 36. It will be useful to first consider the manner in which these calibration curves are obtained. For purposes of example, the application in which the apparatus 10 is used to monitor the manufacture of magnetic recording material will be considered to illustrate the generation of these curves.

As has been noted above, the characteristic of the first radiation beam that is utilized in the present invention is that attenuation of the first radiation beam as it passes through the web 18 is substantially independent of the relative specific weights of the two components of the web. That is, the detector signal produced by the first radiation detector 32 is indicative of the combined specific weights of the two components of the web without regard to the distribution of this combined specific weight between the two components of the web. The function of calibration for the first radiation sensor is to develop a first calibration curve relating the intensity of radiation passing through the web 18 to the total specific weight of the web 18.

To obtain the first calibration curve, which has been indicated at 62 in FIG. 3, a plurality of samples of recording material is obtained and the weight and area of each of these samples is measured to determine the specific weight of each of the samples. A suitable source of the samples is a selection of floppy discs, computer tapes, and other materials which are used in a recording device. After the determination of the specific weight of each sample, each sample is placed in the first radiation beam to attenuate the beam and the first detector signal is noted for each of the samples. In addition, the first detector signal is noted for the situation in which only air is in the first radiation beam so that the quantities which can be related in developing the calibration curve 62 are the specific weights of the samples and the ratio of a detector signal with a sample in the first radiation beam to the intensity of the detector signal with only air in the beam. This ratio, which can be considered to be an intensity ratio for the first radiation beam, is a measure of the attenuation of the first radiation beam in the web 18.

Following this initial set of measurements, each of the samples is stripped of one layer of the magnetic coating by softening such layer with heptane or acetone and rubbing the sample with a material, such as cloth, that is softer than the dielectric substrate. The intensity ratio and specific weight measurements are then repeated and the second side of the sample is then stripped for a further repetition of the intensity ratio and specific weight measurements. The last set of measurements will be for uncoated dielectric. The three sets of measurements are then compared to determine whether the intensity ratio versus specific weight relationships for the three sets of measurements differ significantly. In the absence of a significant difference in the results of the measurements, the relationship between the intensity ratio and the specific weight is independent of the relative specific weights of the two components of the web. The calibration curve 62 is developed by relating the specific weights of all of the samples, before and after coating, to the intensity ratios measured by the first radiation sensor. In particular, the total specific weight of the composite web is written as a fourth order polynomial in the intensity ratio, obtained via a least squares fit of the data taken with the samples of web material, and the microcomputer 54 is programmed with such polynomial relationship.

At the same time that intensity ratio measurements are made on the samples with the first radiation beam, similar intensity ratio measurements are made with the second radiation beam. However, the measurements using the second radiation beam are analyzed in a different manner than the measurements for the first radiation beam to reflect the different characteristic of the second radiation beam that is utilized in the use of the apparatus 10. As noted above, the second radiation source 34 is selected so that the attenuation of the second radiation beam in each of the two components of the web increases exponentially with specific weight of such component and the attenuation coefficients of the two components of the web differ. Based on such characteristic, the final set of intensity ratio versus specific weight measurements; that is, the measurements made after both layers of magnetic coating have been stripped from the samples, is utilized to develop a calibration curve 64 illustrated in FIG. 3. Such calibration curve 64 will be referred to herein as an effective, one-component calibration curve. Such curve relates the attenuation of the second radiation beam to the specific weight of a web comprised solely of the dielectric substrate and, as indicated in FIG. 3, increases exponentially with specific weight of such a one-component web. From the calibration curve 64, and the radiation attenuation measurements made on the samples prior to complete stripping of the layers of the magnetic coating on the samples, another calibration curve, indicated in dashed lines in FIG. 3 and designated by the numeral 66 can be developed relating the attenuation of the second radiation beam to the specific weight of the component of the samples provided by the magnetic coating and, accordingly, of the web 18. In particular, intensity ratio data points for the calibration curve 66 are found by dividing the intensity ratio for each sample obtained before complete stripping of the layers of magnetic coating from the sample by the intensity ratio measured for the sample after both layers have been stripped from the sample. The corresponding specific weight data points are determined from the decrease in sample weight resulting from the stripping of a layer of the magnetic coating from the sample. From the curve 66, the attenuation coefficient for the second radiation beam in the magnetic coating material can be obtained.

Turning now to the method in which the apparatus 10 is used to measure the specific weights of both components of the web 18, the radiation assembly 28 is mounted about the web 18 as has been indicated in FIG. 1 so that, as the web is manufactured, the intensity of both radiation beams can be measured by the detectors 32 and 36 and the detector signals provided by the detectors 32 and 36 are transmitted to the microcomputer 54. Additionally, the detector assembly 28 is periodically driven off the web so that each of the detector signals is provided to the microcomputer 54 for the case in which only air is disposed between the sources and detectors of the two radiation sensors. Thus, the radiation sensors provide the microcomputer with detector signals which are indicative of the attenuation of both the first and second radiation beams in the web 18 as the web 18 is formed.

Initially, in order to provide signals that are indicative of the specific weights of both components of the web 18, the microcomputer utilizes the first detector signal and the calibration curve 62 to determine the total specific weight of the web 18. In particular, if the intensity ratio for the first radiation sensor has the value $R_B$ as indicated in FIG. 3, the first calibration curve 62 will yield the specific weight $W_{ACT}$ indicated in FIG. 3 and such specific weight will be the actual combined specific weights of the two components of the web 18.

To apportion the combined specific weight of the web 18 between the two components thereof, the calibration curve 64 is utilized to determine an effective specific weight for the web 18, such effective specific weight being the specific weight of a one-component web made of the dielectric substrate that would cause the second detector signal to have the observed amplitude. That is, if the intensity ratio that is a measure of the attenuation of the second radiation beam in the web has the value $R_X$ indicated in FIG. 3, the effective specific weight determined from the second calibration curve 64 will have a value indicated at $W_{EFF}$ shown in FIG. 3. Because of the recited characteristics of the second radiation beam, an actual calibration curve for the web using the second radiation detector 36 would have the form of an exponentially decaying curve as shown by the upper dashed curve marked 65 in FIG. 3, such curve indicating the variation with total specific weight of the attenuation of the second radiation beam in a two-component web having a fixed ratio of the two components. The location of this curve will vary with the relative specific weights of the two components of the web so that a family of such curves will exist between the curves 64 and 66 and a web being manufactured in the field can correspond to any one of such a family of curves. If the particular member of this family could be determined, such knowledge along with the total specific weight of the web would yield the specific weights of both components of the web. However, in the conditions of manufacture of the web, the particular member of such family of curves will not be known. The present invention eliminates the need for determining which particular member of the family of curves for the second radiation sensor actually corresponds to the distribution of the specific weight of the web between the two components thereof. Rather, in the present invention, the attenuation of the second radiation beam is related to the one-component calibration curve 64 which was developed using the samples which have been stripped of the magnetic coating. Such curve will yield, for any intensity ratio $R_X$ measured by the second radiation sensor, an effective specific weight of the dielectric that would yield the same intensity ratio for the web. The difference between this effective one-component total specific weight for the web and the actual specific weight for the web can be shown to be related to the specific weight of the second component of the web 18 by the following expression where the recited characteristics of the second radiation beam obtains:

$$W_2 = \left( \frac{\mu_1}{\mu_2 - \mu_1} \right) (W_{EFF} - W_{ACT}), \quad (1)$$

where $W_2$ is the specific weight of the second component of the web, $\mu_1$ is the attenuation coefficient of the second radiation beam in the first component of the web, and $\mu_2$ is the attenuation coefficient of the second radiation beam in the second component of the web. In particular, where the first component of the web is considered to be the dielectric substrate, the above expression gives the specific weight of the magnetic coating on the web. The specific weight of the other component of the web then follows immediately from $W_{ACT}$ and $W_2$ as follows:

$$W_1 = W_{ACT} - W_2. \quad (2)$$

Thus, the signal indicating the relative specific weights of the two components of the web is generated by programming the microcomputer 54 to utilize the first calibration curve 62 to generate a signal indicative of the total specific weight of the web and by programming the microcomputer to utilize the second calibration curve 64 to generate a signal indicative of the specific weight of the second component of the web alone and, from the two specific weights, a signal indicative of the specific weight of the first component of the web. Such signals can be transmitted to a display device or to the actuator assembly 26 to automatically control the manufacture of the web 18.

CROSS TALK SUPPRESSION

While the above described apparatus and method provide a useful way of obtaining signals indicative of the specific weights of both components of a two component web, such method and apparatus can be made inoperable by the occurrence of excessive cross talk between the first and second radiation sensors. That is, the provision of these signals depends upon the detector signals produced by the first and second radiation detectors, 32 and 36 respectively, providing measures of the attenuation of the first and second radiation beams, respectively, in the web 18. Cross talk between the sensors will result in one or both of the detectors providing a signal which is not indicative of the attenuation of the radiation beam directed toward such detector and is especially severe when one of the radiation sensors is a beta sensor and the other of the radiation sensors is an X-ray sensor. In such case, bremstrahlung produced by the attenuation of the beta ray beam can be detected by the X-ray detector to provide a faulty reading of the attenuation of X-ray radiation in the web 18. FIGS. 2 and 4 illustrate the manner in which cross talk is suppressed in the present invention by substantially eliminating such bremstrahlung.

In order to discuss the suppression of cross talk in the present invention, it will be useful to briefly consider the mechanisms by means of which a beta radiation beam is attenuated in matter. A beta particle entering matter composed of elements having low atomic weights can collide with electrons in the matter and be scattered thereby. Such scattering ultimately transfers the energy of the beta particle to heat and low energy electromagnetic radiation. In general, the energy of the radiation thus produced will be too low to be detected by an ionization chamber designed to measure X-rays so that no cross talk is produced by the attenuation of beta radiation by this collision mechanism. However, a beta particle entering matter can also lose energy through an interaction with an atomic nucleus to produce bremstrahlung. In general, the spectrum of the bremstrahlung will shift toward higher energies as the atomic weight of the nucleus with which the beta particle interacts and the energy of the beta particle prior to interaction increase. Thus, if a low energy beta particle enters a material composed of elements having a relatively low atomic weight, the radiation arising from interactions between the particle and nuclei will have little effect on an X-ray detector. However, if a high energy particle enters a material composed of elements having a relatively high atomic weight; for example, aluminum or iron, bremstrahlung will be produced at energies sufficient to be detected by the ionization chamber of an X-ray sensor. Moreover, when a beam of beta radiation is transmitted through a web such as the web 18, scattering of the beam within the web broadens the beam so that scattered beta particles can impinge upon surrounding objects in which the bremstrahlung can be produced to interfere with the X-ray intensity measurements.

In the present invention, bremstrahlung is suppressed by three techniques which have been illustrated in FIG. 2. As can be seen in FIG. 2, a thin film 68 of an organic polymer is mounted on the wall 42 of the source housing 38 to extend across the first beam aperture 44 (the beta ray beam aperture) through which the beam of beta radiation used to determine the total specific weight of the web exits the source housing 38. The effect of the film 68 has been indicated in FIG. 4 in which the solid curve 70 is a schematic representation of the energy spectrum of beta radiation produced by a source used in a beta sensor. When a beam of beta radiation having such a spectrum is transmitted through a film of organic polymer, the beam will be attenuated and, since the polymer is composed of elements having relatively low atomic weights, the attenuation will occur primarily by collision with atomic electrons so that very little bremstrahlung will be produced by the attenuation of the beta radiation beam. The result is that the peak of the energy spectrum of the beta radiation will be shifted toward lower energies while the overall flux of the radiation will be slightly decreased. Such result is indicated by the dashed curve 72 in FIG. 4. One benefit of the shift in the energy spectrum of the beta radiation beam; that is, the "softening" of the radiation beam, is that bremstrahlung produced by subsequent incidence of the beam on a material in which bremstrahlung can be produced will result in a lower intensity for the bremstrahlung. In this regard, it has been observed experimentally that the intensity of bremstrahlung produced by the incidence of a beta radiation beam on a material increases with increasing energy of the radiation beam. A suitable choice for the film 68, where the apparatus 10 is used to monitor the production of magnetic recording material and is comprised of the sources and detectors indicated above, is polyester that is ten thousands of an inch thick and the film 68 can be fastened to the housing wall 42 to extend across the aperture 44 in any convenient manner.

Because of the scattering of the beta radiation beam in the web, and the broadening of the beam caused thereby, beta radiation can impinge on the wall 48 of the detector housing 40 so that bremstrahlung can be produced by the interaction of scattered beta particles with material of which the housing 40 is constructed. This source of bremstrahlung, which can interfere with X-ray attenuation measurements by the sensor assembly 28, is substantially eliminated by a detector housing shield 74 that is interposed between the web 18 and the detector housing 40. The detector housing shield 74 can be made of an organic polymer, such as phenolic, and is preferably mounted directly on the wall 48 of the detector housing 40. By constructing the detector housing shield of an organic polymer, the scattered beta particles lose energy within the shield 74 primarily by means of the collision process so that very little bremstrahlung is produced within the shield 74. It has been found that a shield made of phenolic having a thickness of approximately one eighth inch is sufficient to stop any beta radiation scattered from the web 18 before such radiation reaches the detector housing 40 to substantially eliminate this source of bremstrahlung that might interfere with the X-ray attenuation measurements.

In order that the two radiation beams can pass through the detector housing shield 74, the detector housing shield is provided with a first radiation beam aperture 76 (a beta ray beam aperture) that is aligned with the first radiation beam aperture 50 through the wall 48 of the detector housing 40 and a second radiation beam aperture 78 (an X-ray beam aperture) that is aligned with the second radiation beam aperture 52 (the X-ray beam aperture) through the wall 48 of the detector housing 40. The X-ray beam aperture 78 formed through the detector housing shield 74 is shaped in the present invention to effect a further reduction in cross talk between the two radiation sensors arising from bremstrahlung produced by the first radiation beam; that is, the beta radiation beam. In particular, the X-ray beam aperture 78 through the detector housing shield 74 is made smaller than the second radiation beam aperture 52 through the wall 48 of the detector housing in order to limit the directions from which an X-ray photon can enter the detector housing 40 and be counted by the second detector 36. A particularly useful method of shaping the X-ray beam aperture 78 through the detector shield housing 40 is to reduce the contours of the second radiation beam aperture 78 of the detector housing shield 74 to the point that portions of the detector housing shield 74 begin to limit the intensity of X-ray radiation reaching the second detector 36. That is, a shutter is placed over the beta ray beam aperture 44 of the source housing so that the second detector can receive X-rays only from the X-ray source 34 and pieces of phenolic are placed on the wall 48 of the detector housing 40 to limit the opening through the X-ray beam aperture 52 into the detector housing 40 until the detector signal produced by the second radiation sensor; that is, the X-ray radiation sensor, is decreased by the placement of the phenolic on the housing 40. The resulting opening through the pieces of phenolic above the X-ray beam aperture 52 through the wall 48 of the detector housing 42 is then copied into the X-ray beam aperture 78 through the detector housing shield 74.

It has also been found that bremstrahlung can be produced within the detector housing and the present invention further contemplates the suppression of such bremstrahlung to further reduce cross talk between the two radiation sensors in the apparatus 10. In particular, ionization chambers suitable for use in beta sensors are provided with a thin stainless steel window through which the beta radiation enters the ionization chamber. It has been found that these windows can provide a source of bremstrahlung within the detector housing 40 and the bremstrahlung produced can be sensed by an X-ray radiation detector. Such bremstrahlung is suppressed by means of a further softening of the beta radiation beam by means of a second film 80 of an organic polymer; for example, polyester, that is placed across the beta ray beam aperture 50 through the wall 48 of the detector housing 40. As in the case of the film 68 placed across the beta ray beam aperture 48 through the wall 42 of the source housing 38, the film 80 can be mounted on the wall 48 by fastening the film 80 across the aperture 50 in any convenient manner. Similarly, a sufficient thickness for the film 80 which will provide adequate beam softening without significantly interfering with the operation of the first radiation sensor; that is, the beta sensor used in the preferred application of the present invention, is ten thousandths of an inch thick. It has been found that the use of the films 78 and 80, the use of the detector housing shield 74 and the restriction of the X-ray beam aperture 78 through the detector housing shield 74 can reduce the intensity of bremstrahlung produced by a beta radiation beam by 86% which is sufficient to enable the apparatus 10 to accurately provide signals indicative of the relative specific weights of a web of magnetic recording material.

It is clear that the present invention is well adapted to carry out the objects and attain the ends and advantages mentioned as well as those inherent therein. While a presently preferred embodiment of the invention has been described for purposes of this disclosure, numerous changes can be made which will readily suggest themselves to those skilled in the art and which are encompassed within the spirit of the invention disclosed and as defined in the appended claims.

We claim:

1. An apparatus for generating signals indicative of the specific weight of both components of a layered, two-component web, comprising:
    a first radiation sensor for providing a first detector signal indicative of the total specific weight of the web, the first radiation sensor comprising a first radiation detector and means for directing a first radiation beam through the finished web to the first radiation detector so that the first detector signal provides a measure of the attenuation of the first radiation beam by the web;
    a second radiation sensor for providing a second detector signal indicative of an effective, one-component specific weight of the web, the second radiation sensor comprising a second radiation detector and means for directing a second radiation beam through the finished web to the second radiation detector so that the second detector signal provides a measure of the attenuation of the second radiation beam by the web; and
    computer means, connected to the radiation sensors, for generating said signals indicative of the specific weights of the web components in response to reception of said detector signals by the computer means; wherein the first radiation beam is characterized in that the attenuation of the first radiation beam in the web is substantially independent of the relative specific weights of the two components of the web; and wherein the second radiation beam is characterized in that the intensity of the second radiation beam decays exponentially in both components of the web with the attenuation coefficient of the second radiation beam for one component of the web differing from the attenuation coefficient of the second radiation beam for the other component of the web.

2. The apparatus of claim 1 wherein said web is comprised of at least one layer of binder containing a magnetic material on a dielectric substrate; wherein the means for directing a first radiation beam through the finished web comprises a beta radiation source having a minimum particle energy of about 0.07 mev and a maximum particle energy of about 0.6 mev; and wherein the means for directing a second radiation beam through the finished web comprises an X-ray radiation source having a minimum energy of about 3.5 kev and maximum energy of about 15.0 kev.

3. The apparatus of claim 2 wherein the X-ray source is an iron 55 encapsulated isotopic source.

4. The apparatus of claim 1 wherein the second radiation detector is characterized as being responsive to X-Ray radiation; wherein the first radiation sensor comprises a beta ray source to provide said first radiation beam; and wherein the apparatus further comprises means for suppressing the production of bremstrahlung by the first radiation beam.

5. The apparatus of claim 4 wherein the beta ray source is disposed in a source housing having a first beam aperture through which the first radiation beam exits the source housing formed through one wall thereof facing one side of the web; and wherein the means for suppressing the production of bremstrahlung comprises a film of organic polymer placed across the first beam aperture.

6. The apparatus of claim 5 wherein the first radiation detector is disposed in a detector housing positioned on the other side of the web; and wherein the means for suppressing the production of bremstrahlung comprises a detector housing shield interposed between the web and the detector housing, said shield having the form of a sheet of organic polymer having a first beam aperture formed therethrough in alignment with the first beam aperture formed through said one wall of the source housing.

7. The apparatus of claim 6 wherein a first beam aperture is formed through one wall of the detector housing facing the web for entry of the first radiation beam into the detector housing; and wherein the means for suppressing the production of bremstrahlung further comprises a film of organic polymer placed across the first beam aperture formed through the wall of the detector housing.

8. The apparatus of claim 4 wherein the beta ray source is disposed in a source housing having a first beam aperture through which the first radiation beam exits the source housing formed through one wall thereof facing one side of the web; wherein the first radiation detector is disposed in a detector housing positioned on the other side of the web; and wherein the means for suppressing the production of bremstrahlung comprises a detector housing shield interposed between the web and the detector housing, the detector housing shield having the form of a sheet of organic polymer having a first beam aperture formed therethrough in alignment with the first beam aperture formed through said one side of the source housing.

9. The apparatus of claim 8 wherein a first beam aperture is formed through one wall of the detector housing facing the web for entry of the first radiation beam into the detector housing; and wherein the means for suppressing the production of bremstrahlung further comprises a film of organic polymer placed across the first beam aperture formed through the wall of the detector housing.

10. The apparatus of claim 4 wherein the beta ray source is disposed in a source housing having a first beam aperture through which the first radiation beam exits the source housing formed through one wall thereof facing one side of the web; wherein the first radiation detector is disposed in a detector housing positioned on the other side of the web and having a first beam aperture formed through one wall thereof facing the web and aligned with the first beam aperture of the source housing; and wherein the means for suppressing the production of bremstrahlung by the first radiation beam comprises a film of organic polymer placed across the first beam aperture formed through the wall of the detector housing.

11. The apparatus of claim 10 wherein the means for suppressing the production of bremstrahlung by the first radiation beam further comprises a film of organic polymer placed across the first beam aperture of the source housing.

12. The apparatus of claim 1 wherein the first radiation sensor comprises a beta ray source to provide said first radiation beam and the second radiation sensor comprises an X-ray source to provide said second radiation beam; wherein the apparatus further comprises:
  a source housing wherein said sources are disposed, the source housing having a first beam aperture, through which the first radiation beam exits the source housing, and a second beam aperture, through which the second radiation beam exits the source housing, formed through one wall thereof facing one side of the web;
  a detector housing positioned on the other side of the web and containing said first and second radiaton detectors, the detector housing having a first beam aperture through which the first radiation beam enters the detector housing and a second beam aperture through which the second radiation beam enters the detector housing formed through the wall of the detector housing facing the web; and
  means for suppressing the production of bremstrahlung by the first radiation beam.

13. The apparatus of claim 12 wherein the means for suppressing the production of bremstrahlung comprises a film of organic polymer placed across the first beam aperture of the source housing.

14. The apparatus of claim 13 wherein the means for suppressing the production of bremstrahlung further comprises a detector housing shield interposed between the web and the detector housing, said shield having the form of a sheet of organic polymer having first and second beam apertures formed therethrough in alignment with the first and second beam apertures formed through the wall of the detector housing.

15. The apparatus of claim 14 wherein the means for suppressing the production of bremstrahlung further comprises a film of organic polymer placed across the first beam aperture of the detector housing.

16. The apparatus of claim 15 wherein the second beam aperture formed through the detector housing shield is smaller than the second beam aperture formed through one wall of the detector housing.

17. The apparatus of claim 14 wherein the second beam aperture formed through the detector housing shield is smaller than the second beam aperture formed through one wall of the detector housing shield.

18. The apparatus of claim 12 wherein the means for suppressing the production of bremstrahlung by the first radiation beam comprises a detector housing shield interposed between the web and the detector housing, said shield having the form of a sheet of organic polymer having a first beam aperture formed therethrough in alignment with the first beam aperture formed through one wall of the detector housing and a second beam aperture formed therethrough in alignment with the second beam aperture formed through one wall of the detector housing.

19. The apparatus of claim 18 wherein the means for suppressing the production of bremstrahlung further comprises a film of organic polymer disposed across the first beam aperture formed through the detector housing shield.

20. The apparatus of claim 18 wherein the second beam aperture formed through the detector housing shield is smaller than the second beam aperture formed through one wall of the detector housing.

21. The aparatus of claim 12 wherein the means for suppressing the production of bremstrahlung by the first radiation beam comprises a film of organic polymer placed across the first beam aperture of the detector housing.

22. The apparatus of claim 21 wherein the means for suppressing the production of bremstrahlung by the first radiation beam further comprises a film of organic polymer placed across the first beam aperture of the source housing.

23. A system for suppressing the production of bremstrahlung in a radiation sensor assembly including a beta ray sensor and an X-ray sensor, each of said sensors comprising a radiation source located in an assembly source housing and a radiation detector located in an assembly detector housing, said housings disposed in a generally parallel, spaced-apart relation and each of said housings having a beta ray beam aperture and an X-ray beam aperture formed through one wall thereof facing the other housing to provide radiation paths between the source and detector of each sensor, the system for suppressing the production of bremstrahlung comprising:
  a film of organic polymer extending across the beta ray beam aperture formed through said wall of the source housing.

24. The system of claim 23 further comprising a detector housing shield having the form of a sheet of organic polymer overlaying the wall of the detector housing through which the beta ray beam aperture and X-ray beam aperture are formed, the detector housing shield having a beta ray beam aperture aligned with the beta ray beam aperture of the detector housing and an X-ray beam aperture aligned with the X-ray beam aperture of the detector housing.

25. The system of claim 24 further comprising a film of organic polymer extending across the beta ray beam aperture of the detector housing.

26. The system of claim 25 wherein the X-ray beam aperture formed through the detector housing shield is smaller than the X-ray beam aperture formed through the wall of the detector housing.

27. The system of claim 24 wherein the X-ray beam aperture formed through the detector housing shield is smaller than the X-ray beam aperture formed through the wall of the detector housing.

28. The system of claim 23 further comprising a film of organic polymer extending across the beta ray beam aperture formed through said wall of the detector housing.

29. A system for suppressing the production of bremstrahlung in a radiation sensor assembly including a beta ray sensor and an X-ray sensor, each of said sensors comprising a radiation source located in an assembly source housing and a radiation detector located in an assembly detector housing, said housings disposed in a generally parallel, spaced-apart relation and each of said housings having a beta ray beam aperture and an X-ray beam aperture formed through one wall thereof facing the other housing to provide radiation paths between the source and detector of each sensor, the system for suppressing the production of bremstrahlung comprising:
  a detector housing shield having the form of a sheet of organic polymer overlaying the wall of the detector housing through which the beta ray beam aperture and X-ray beam aperture are formed, the detector housing shield having a beta ray beam aperture aligned with the beta ray beam aperture of the detector housing and an X-ray beam aperture aligned with the X-ray beam aperture of the detector housing.

30. The system of claim 29 further comprising a film of organic polymer extending across the beta ray beam aperture of the detector housing.

31. The system of claim 29 wherein the X-ray beam aperture formed through the detector housing shield is smaller than the X-ray beam aperture formed through the wall of the detector housing.

32. A system for suppressing the production of bremstrahlung in a radiation sensor assembly including a beta ray sensor and an X-ray sensor, each of said sensors comprising a radiation source located in an assembly source housing and a radiation detector located in an assembly detector housing, said housings disposed in a generally parallel, spaced-apart relation and each of said housings having a beta ray beam aperture and an X-ray beam aperture formed through one wall thereof facing the other housing to provide radiation paths between the source and detector of each sensor, the system for suppressing the production of bremstrahlung comprising:
a film of organic polymer extending across the beta ray beam aperture formed through said one wall of the detector housing.

33. A method for generating signals indicative of the specific weights of both components of a layered, two component web, comprising the steps of:
passing a first radiation beam through the web to a first radiation detector, the first radiation detector providing a first detector signal indicative of the intensity of the first radiation beam received thereby, wherein the first radiation beam is characterized in that attenuation of the intensity thereof via passage of the first radiation beam through the web is substantially independent of the relative specific weights of the two components of the web;
passing a second radiation beam through the web to a second radiation detector, the second radiation detector providing a second detector signal indicative of the intensity of the second radiation beam received thereby, wherein the second radiation beam is characterized in that the intensity of the second radiation beam decays exponentially in both components of the web with the attenuation coefficient of the second radiation beam for one component of the web differing from the attenuation coefficient of the second radiation beam for the other component of the web; and
generating said signals indicative of the specific weights of the web components from the first and second detector signals.

34. The method of claim 33 further comprising the steps of:
developinig a first calibration curve relating the first detector signal to the total specific weight of the web;
developing a second calibration curve relating the second detector signal to the specific weight of a web composed of only one of the two components of the two component web; and
determining the attentuation coefficient for the second radiation beam in the material of which the second component of the two component web is composed; and wherein the step of generating signals indicative of the specific weights of the web components from the first and second detector signals comprises the steps of:
determining the total specific weight of the web from the first detector signal and the first calibration curve;
determining the relative specific weights of the two web components from the second calibration curve, the second detector signal, and the attenuation coefficient for the second radiation beam in the material of which the second component of the two component web is composed; and
generating the signals indicative of the specific weights of the web components from the total specific weight and relative specific weights of the web.

35. The method of claim 34 wherein the step of developing a first calibration curve is comprised of the steps of:
obtaining a plurality of samples of the two component web;
measuring the total specific weight of each of said plurality of samples;
passing the first radiation beam through each of said samples; and
measuring the attenuation of the first radiation beam caused by passage of the first radiation beam through said samples.

36. The method of claim 35 wherein the step of developing a second calibration curve comprises the steps of:
stripping said second component of the two component web from each of said samples;
measuring the specific weights of each of said samples after the stripping of said second component from the samples;
passing the second radiation beam through each of said samples; and
measuring the attenuation of the second radiation beam by each of said samples.

37. The method of claim 36 wherein the step of determining the attenuation coefficient for the second radiation beam in the material of which the second component of the two component web is composed is comprised of the steps of:
passing the second radiation beam through each of said samples prior to stripping the second component from each of said samples;
determining the specific weight of said second component for each of said samples from the decrease in specific weight of each sample resulting from the stripping of said second component;
determining the attenuation of the second radiation beam in said second component from the difference in the attenuation of the second radiation beam for each sample before and after the stripping of said second component; and
developing a third calibration curve from the specific weights of the second component in each of said samples and the attenuation of the second radiation beam in the second component of each of said samples.

38. The method of claim 36 wherein said one component of the web is a dielectric and said second component of the web is a binder containing a magnetic material; and wherein the step of stripping the second component of the web from each of said samples comprises the softening of the second component of the web with one of heptane and acetone while rubbing the sample with a material softer than the dielectric.

* * * * *